Figure 1:
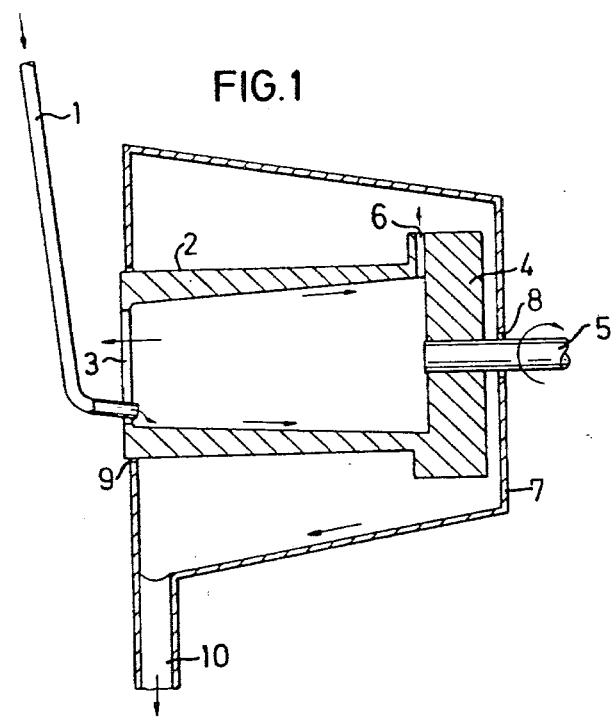

United States Patent [19]

Wegstedt

[11] 4,324,557
[45] Apr. 13, 1982

[54] METHOD AND APPARATUS FOR DEGASSING AND ANALYSIS OF FOAMING LIQUIDS

[75] Inventor: Gunnar L. Wegstedt, Järfälla, Sweden

[73] Assignee: Servochem AB, Vallingby, Sweden

[21] Appl. No.: 99,505

[22] Filed: Dec. 3, 1979

[30] Foreign Application Priority Data

Dec. 14, 1978 [SE] Sweden ............................. 7812850

[51] Int. Cl.³ .................. G01N 9/30; G01N 31/12
[52] U.S. Cl. ............................ 23/232 R; 23/230 R;
422/68; 422/72; 422/80; 422/83; 233/DIG. 1;
233/31; 55/47; 55/203
[58] Field of Search .................... 422/62, 68, 72, 83,
422/101, 80; 23/230 R, 232 R; 73/23; 55/201,
203, 46, 47; 233/27, 31, 37, 43, DIG. 1;
210/184, 203

[56] References Cited

U.S. PATENT DOCUMENTS

| | | | |
|---|---|---|---|
| 2,792,072 | 5/1957 | Moore | 55/203 |
| 3,274,756 | 9/1966 | Stern | 55/47 |
| 3,342,019 | 9/1967 | Smythe | 55/201 |
| 3,973,930 | 8/1976 | Burgess | 55/203 |
| 4,030,897 | 6/1977 | Pelzer et al. | 55/203 |
| 4,113,452 | 9/1978 | Brown et al. | 55/203 |
| 4,182,480 | 1/1980 | Theyse et al. | 233/DIG. 1 |

FOREIGN PATENT DOCUMENTS 7502084  7/1977  Sweden .

*Primary Examiner*—William F. Smith
*Assistant Examiner*—Chris Konkol
*Attorney, Agent, or Firm*—Young & Thompson

[57] ABSTRACT

By using centrifugal force, foaming liquids are degassed and the amount of certain liquid components determined by analyzing exiting gas. Liquid fed to a rapidly rotating beaker is spread as a thin film while gas is forced out without foaming. This film is pressed to the beaker bottom and out through holes to the inside of a casing from where it runs out for collection. Air is blown into the beaker, whose interior is divided by a baffle. A minor amount of air exits through an annular gap between the baffle plate and the beaker wall, and a major amount through a blow-out tube. Volatile airborne liquid components are then analyzed.

5 Claims, 2 Drawing Figures

METHOD AND APPARATUS FOR DEGASSING AND ANALYSIS OF FOAMING LIQUIDS

Foam formation can cause problems in various chemical and physical processes, such as boiling, distilling, mixing etc. One remedy to the foam problem has been to use socalled antifoaming agents which, when added, break down the foam; and, where for some reason antifoaming agents cannot be used, mechanical means are used to prevent foam formation or remove the foam. For example, in distilling, baffles can be arranged which the vapors strike against and remove the gases. It is also possible to arrange the baffle so that the vapors will have a tangential movement and the liquid particles will be thrown against a wall. Centrifugal separators of this type make improved separation possible with smaller pressure losses than the "impinging" separators, and for heavily foaming liquids it is possible to couple two separators in series to achieve in this way sufficient foam separation.

Among the liquids presenting foam problems is beer, which more than all other beverages characteristically has a very stable foam. This foam or head is a criterion for the quality of the beer when served, but in analyses and tests of beer quality, for example, the foam makes it difficult to obtain prompt analytical results.

The foam volume is essentially a function of the carbon dioxide content, and a beer which contains much carbon dioxide also generates much foam. The solubility of carbon dioxide is somewhat less in beer than in water, but through secondary fermentation a supersaturation occurs so that the carbon dioxide content in the beer is about 0.40%.

The beer foam is very stable due to the surfactant substances in the beer, which are concentrated in the foam and form films around the carbon dioxide bubbles. The foam can be broken down by addition of certain substances, such as higher alcohols, soaps, fat, etc. but such additives are not suitable for beer analysis, where many values are required to define the chemical nature of the beer and additives can distort the results. It is usual to determine, for example, pH, acidity, alkalinity, buffering, volatile acids, total nitrogen, formol nitrogen, ammonia nitrogen, total phosphorus, organic phosphorus, etc.

Most of these analyses require that the beer be freed of most of its carbon dioxide. This is most commonly done now by shaking the beer in shaking flasks in a shaking table for fifteen to thirty minutes, or by filtering or stirring the beer. All of these methods are complicated and time-consuming, and attempts to speed them up are halted by the heavy foaming. With older analytical techniques, where each analysis took a long time to perform, the degassing time was of little importance, but rapid, automatic methods now coming into use for process control, have made the time consumption for degassing a serious disadvantage.

The present invention relates to a method of degassing foaming liquids for analysis and an apparatus for degassing of the liquids for analysis.

Figure 2:
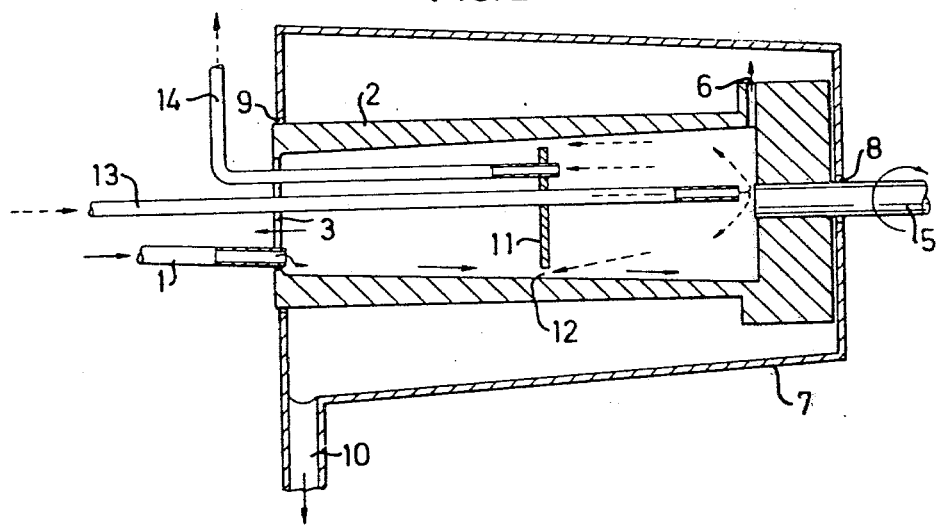

The invention will be described in detail with reference to the accompanying drawing, in which FIG. 1 shows a degassing device according to the invention in section, and FIG. 2 shows an embodiment which makes possible the determination of one or several components in the liquid simultaneously with the degassing.

The latter embodiment has been especially applicable to beer, but it can also be used for other foaming liquids.

Liquid which is to be degassed flows into the apparatus shown in FIG. 1 through the tube 1 and runs out onto the inside of a horizontal, rotating cylindrical beaker 2. The inside of the beaker is slightly conical with a smaller diameter at the opening 3 than at the bottom 4. At the center of the bottom 4, the beaker is fixed to a shaft 5, which is driven by a motor (not shown). Immediately next to the bottom of the beaker, the walls are perforated by three or more symmetrically arranged holes 6.

The rotating beaker 2 is surrounded by a stationary casing 7 shaped as a truncated cone, lying on its side, with its bottom surface in line with the opening 3 of the beaker 2, with a hole 8 in the top surface for the drive shaft 5 and a hole 9 in the bottom corresponding to the opening 3 of the beaker. At the lowest point of the casing there is arranged an outlet tube 10 for degassed liquid.

When the liquid from the tube 1 comes into contact with the rapidly rotating beaker and is spread out into a thin layer by the strong centrifugal force, it is subjected to a powerful mechanical action which releases a large portion of the gas, which flows out through the opening 3 of the beaker. The centrifugal force also causes the liquid to move towards the bottom of the beaker and the outlet holes 6, at the same time as the remaining gas is forced out of the liquid. The thickness of the layer of liquid is determined by the inclination of the cone and the rotational speed of the beaker. A suitable liquid film of ordinary, low-viscosity liquids was found to be formed at 3000–4000 r.p.m. and an inclination of the interior wall of 1/100 to 5/100.

From the holes 6, the liquid is thrown hard against the casing 7 where, due to the powerful striking effect, it is made to release any remaining additional gas. The liquid then runs as a thin film to the outlet 10 where it can be collected.

The apparatus according to the invention achieves in a very short time a complete degassing of a sufficient amount of liquid for analysis free from foam formation. With beer, for example, a volume of 300 ml/min. is fed in, producing in 20 seconds a sample of 100 ml; more than sufficient for both analysis and process control tests.

FIG. 2 shows an embodiment of the invention, especially designed for beer, which in addition to degassing the beer, can also be used to determine the alcohol content. In addition to the parts shown in FIG. 1 and which have corresponding reference numerals, this apparatus is also provided with a circular baffle plate 11 between the bottom 4 of the beaker and the opening 3. The baffle plate defines an interior chamber in the beaker and has a diameter less than the interior diameter of the rotating beaker, so that an annular gap 12 is formed between the plate and the wall. A tube 13 extends through the center of the plate, for blowing in air, and it opens quite close to the bottom 4. Furthermore, above the air tube 13 there is a suction tube 14 with an opening inside the baffle plate 11, to draw out a mixture of air and vapors. In operation, beer is supplied through the tube 1 and runs out onto the interior wall of the rotating beaker inside the opening 3 where it is spread in a thin layer which, in the form of a film, moves along the interior wall through the annular gap 12 towards the bottom 4 and the outlet hole 6. Most of the carbon dioxide is removed before the annular gap 12 and flows out through the opening 3. In the inner chamber, which is bounded by the baffle plate 11, air is blown in through the tube 13 and this creates a very turbulent flow which carries with it alcohol vapors, water vapor and possibly carbon dioxide from the beer film. This mixture exits primarily through the blow-out tube 14. The alcohol content in the outgoing mixture depends on the size of the liquid surface, the temperature, the incoming amount of air and the leakage around the annular gap. In the steady state when the rotational speed, the temperature, the incoming air flow and the beer inflow are kept constant, the liquid surface and the size of the annular gap, which depends on the thickness of the beer film, will also be constant and an equilibrium condition will be created in which the alcohol content in the outgoing air is proportional to the alcohol content of the beer and can be determined exactly with known methods of analysis, e.g. Alcotrol from ServoChem.

Practical tests have shown it to be suitable to use a beer input of 10 ml/min., a rotational speed of 3000 r.p.m. and an incoming amount of air of 8 l/hour. The outflowing mixture of air, alcohol vapor, water vapor and carbon dioxide through the outlet tube 14 was then 7 l/hour. It was also found that when the ratio between the size of the liquid surface and the air flow was sufficiently great, the numerical results were not affected by air flow variations within fairly broad limits. Thus the alcohol content of beer can be determined with good precision at the same time as beer samples are degassed for other analyses.

Similar double functions of the apparatus according to the invention are also possible for other liquids than beer, involving both the removal of a gas and the vaporization and measurement of another component in the liquid. The apparatus can also be modified in various ways, with temperature control of the rotor, multiple rotor cylinders, possibly with fixed baffles therebetween, vertical or tipped beakers, etc. using the same inventive principle.

What I claim is:

1. A method of analysis of foaming liquids, comprising spreading a foaming liquid in a thin film by centrifugal force in a container shaped as a figure of revolution by rotating the container about its axis, blowing air into the container thereby to enrich the air in a component of the liquid to be measured, removing from the container and analyzing the thus-enriched air, said container having a slightly conical internal wall, introducing the liquid to be degassed at the small end of the conical wall, removing degassed liquid from adjacent the large end of the conical wall, removing foam from adjacent the small end of the conical wall, and introducing said air into the container and removing said enriched air from the container a substantial distance from said small end of said conical wall.

2. A method as claimed in claim 1, and introducing said liquid eccentrically of the axis of said conical wall.

3. Apparatus for degassing a foaming liquid, comprising a horizontal rotating container having a slightly conical inner wall, means to introduce liquid to be degassed adjacent the small end of said conical wall, means to remove degassed liquid from adjacent the large end of said conical wall, means to remove gas for analysis from said container, and means for blowing in air into the interior of said container, the point of introduction of said blown in air and the point of removal of said gas for analysis being spaced a substantial distance from the small end of said container.

4. Apparatus as claimed in claim 3, and a circular stationary baffle plate spaced a substantial distance from said small end of the container but closer to said small end of the container than said points of introduction and removal of said blown in air and gas for analysis, there being an annular gap between the baffle plate and said conical wall to allow passage of liquid from the small end of said conical wall toward the large end of said conical wall.

5. Apparatus as claimed in claim 3, said means for introducing liquid to be degassed being disposed eccentrically of the axis of said conical wall.

* * * * *